(12) United States Patent
Librot et al.

(10) Patent No.: US 12,220,317 B2
(45) Date of Patent: Feb. 11, 2025

(54) IMPLANT WITH ABILITY TO CAPTURE EXTRAVASATING FIXATION MEDIUM (71) Applicant: Onkos Surgical, Inc., Parsippany, NJ (US)

(72) Inventors: Dan Librot, Westwood, NJ (US); Aaron Markworth, Flanders, NJ (US); Mike King, Bernardsville, NJ (US)

(73) Assignee: ONKOS SURGICAL, INC., Parsippany, NJ (US)

( * ) Notice: Subject to any disclaimer, the term of this patent is extended or adjusted under 35 U.S.C. 154(b) by 64 days.

(21) Appl. No.: 17/742,773

(22) Filed: May 12, 2022

(65) Prior Publication Data
US 2022/0265430 A1 Aug. 25, 2022

Related U.S. Application Data (62) Division of application No. 16/798,825, filed on Feb. 24, 2020, now abandoned, which is a division of
(Continued)

(51) Int. Cl.
A61F 2/30 (2006.01)
A61F 2/36 (2006.01)
(Continued)

(52) U.S. Cl.
CPC ...... A61F 2/30771 (2013.01); A61F 2/30728 (2013.01); A61F 2/36 (2013.01); A61F 2/38 (2013.01); A61F 2002/30332 (2013.01); A61F 2002/30405 (2013.01); A61F 2002/30507 (2013.01); A61F 2002/30667 (2013.01);
(Continued)

(58) Field of Classification Search
None
See application file for complete search history.

(56) References Cited

U.S. PATENT DOCUMENTS 3,987,499 A   10/1976  Scharbach et al.
4,524,467 A *  6/1985  DeCarlo, Jr. ............. A61F 2/32
                                              623/19.12
(Continued)

FOREIGN PATENT DOCUMENTS

DE   202006014950 U1   2/2008
DE   102006047663 A1   4/2008
(Continued)

OTHER PUBLICATIONS

G.J.C. Myers, et al., Endoprosthetic replacement of the distal femur for bone tumours; Long-Term Results; The Journal of Bone and Joint Surgery; vol. 89-B, No. 4, Apr. 2007; pp. 6.
(Continued)

Primary Examiner — Ann Schillinger
(74) Attorney, Agent, or Firm — Corner Counsel, LLC (57) ABSTRACT A surgical implant with recesses adapted to capture fixation medium that extravasates during implantation. The implant includes an elongated stem having a distal tip configured for insertion into an implant receiving area of a patient. A collar having recesses for capturing extravasating fixation medium is attached on the stem. The collar can be fixed to the stem by a separable collar-engagement feature or the collar can be fixed to the stem via structures on the stem.

16 Claims, 9 Drawing Sheets

Related U.S. Application Data application No. 15/853,743, filed on Dec. 23, 2017, now Pat. No. 10,610,365.

(51) Int. Cl.
*A61F 2/38* (2006.01)
*A61F 2/46* (2006.01)

(52) U.S. Cl.
CPC ............ *A61F 2002/30729* (2013.01); *A61F 2002/30795* (2013.01); *A61F 2002/30828* (2013.01); *A61F 2002/3093* (2013.01); *A61F 2002/4631* (2013.01); *A61F 2220/0008* (2013.01)

(56) References Cited

U.S. PATENT DOCUMENTS

| | | | |
|---|---|---|---|
| 4,623,349 A | 11/1986 | Lord | |
| 4,822,366 A | 4/1989 | Bolesky | |
| 4,878,917 A | 11/1989 | Kranz et al. | |
| 4,963,155 A | 10/1990 | Lazzeri et al. | |
| 5,002,578 A | 3/1991 | Luman | |
| 5,163,964 A | 11/1992 | Lazzeri et al. | |
| 5,201,767 A | 4/1993 | Caldarise et al. | |
| 5,658,349 A | 8/1997 | Brooks et al. | |
| 5,702,453 A * | 12/1997 | Rabbe | A61F 2/30744 606/264 |
| 5,755,793 A * | 5/1998 | Smith | A61F 2/30734 623/23.48 |
| 6,001,098 A | 12/1999 | Metz-Stavenhagen et al. | |
| 6,048,365 A | 4/2000 | Burrows et al. | |
| 6,071,311 A | 6/2000 | O'Neil et al. | |
| 6,228,120 B1* | 5/2001 | Leonard | A61F 2/4612 623/19.12 |
| 6,344,060 B1 | 2/2002 | Schmotzer et al. | |
| 6,613,092 B1 | 9/2003 | Kana et al. | |
| 6,652,589 B2 | 11/2003 | Schmotzer et al. | |
| 6,682,568 B2 | 1/2004 | Despres, III et al. | |
| 6,706,072 B2 | 3/2004 | Dwyer et al. | |
| 7,044,976 B2 | 5/2006 | Meswania | |
| 7,097,663 B1* | 8/2006 | Nicol | A61F 2/4014 623/19.12 |
| 7,141,073 B2* | 11/2006 | May | A61B 17/1725 623/32 |
| 7,291,174 B2* | 11/2007 | German | A61F 2/30734 623/23.46 |
| 7,544,211 B2* | 6/2009 | Rochetin | A61F 2/389 623/20.15 |
| 7,662,189 B2 | 2/2010 | Meswania | |
| 7,785,371 B2* | 8/2010 | Collazo | A61F 2/4014 623/23.42 |
| 8,021,433 B2 | 9/2011 | Meswania et al. | |
| 8,118,868 B2* | 2/2012 | May | A61F 2/367 623/13.14 |
| 8,172,906 B2* | 5/2012 | Yang | A61F 2/3607 623/23.46 |
| 8,226,725 B2 | 7/2012 | Ferko | |
| 8,337,205 B2* | 12/2012 | Reed | A61C 8/0086 433/174 |
| 8,535,386 B2* | 9/2013 | Servidio | A61F 2/30767 623/23.46 |
| D699,850 S | 2/2014 | Meswania et al. | |
| 8,641,773 B2 | 2/2014 | Bergin et al. | |
| 8,702,804 B2* | 4/2014 | Smith | A61F 2/4014 623/23.11 |
| 8,771,362 B2* | 7/2014 | Isch | F16B 5/0275 623/22.15 |
| 8,900,317 B2* | 12/2014 | Zubok | A61F 2/30734 623/20.32 |
| 8,926,708 B2 | 1/2015 | Servidio et al. | |
| 9,005,305 B2 | 4/2015 | Meyers et al. | |
| 9,345,580 B2 | 5/2016 | Porter et al. | |
| 9,398,928 B2* | 7/2016 | Chavarria | A61F 2/40 |
| 9,463,090 B2 | 10/2016 | Meswania et al. | |
| 9,622,870 B2* | 4/2017 | Ekelund | A61F 2/4637 |
| 9,668,758 B2* | 6/2017 | Collazo | A61F 2/30724 |
| 10,136,923 B2* | 11/2018 | Keyer | A61B 17/8841 |
| 10,463,402 B2* | 11/2019 | Biester | A61B 17/7007 |
| 10,610,365 B2* | 4/2020 | Librot | A61F 2/30771 |
| 11,172,940 B2* | 11/2021 | Servidio | A61B 17/175 |
| 11,357,631 B2* | 6/2022 | Bauer | A61F 2/30723 |
| 2004/0162619 A1* | 8/2004 | Blaylock | A61F 2/30734 606/88 |
| 2006/0015188 A1 | 1/2006 | Grimes | |
| 2007/0179628 A1 | 8/2007 | Rochetin | |
| 2008/0221622 A1* | 9/2008 | Triplett | A61F 2/4684 606/264 |
| 2011/0054625 A1 | 3/2011 | Ferko et al. | |
| 2012/0016482 A1* | 1/2012 | Mooradian | A61F 2/30734 623/18.11 |
| 2012/0116521 A1 | 5/2012 | Meswania et al. | |
| 2013/0030540 A1 | 1/2013 | Leibinger | |
| 2014/0330274 A1* | 11/2014 | Matityahu | A61B 17/748 606/304 |
| 2015/0351940 A1* | 12/2015 | Lacraz | A61F 2/2814 623/16.11 |
| 2018/0200061 A1 | 7/2018 | Bauer | |

FOREIGN PATENT DOCUMENTS

| | | | |
|---|---|---|---|
| EP | 1269937 A2 | 1/2003 | |
| WO | WO-2007025132 A2 * | 3/2007 | ............ A61B 17/56 |
| WO | 2017005512 | 1/2017 | |

OTHER PUBLICATIONS

Melanie J. Coathup BSc, PhD, et al., Hydroxyapatite-coated Collars Reduce Radiolucent Line Progression in Cemented Distal Femoral Bone Tumor Implants; Clinical Orthopaedics and Related Research; Aspectic Loosening of Bone Tumor Prostheses; vol. 473, No. 4, Apr. 2015; pp. 1505-1514.

Stryker Orthopaedics, GMRS (Global Modular Replacement System), One System, One Vision Made for Life; Literature No. LGMRSB Rev.1; 2004, pp. 13.

Wright Medical Technology, Inc., Oncology Solutions; Guardian Limb Salvage System; 2003, pp. 4.

Stanmore Implants, AdHAesio HA Collar Technology; 2016, 1 Page.

Zimmer Segmental System, Simple solutions for solving complex salvage cases; A Step Forward; 97-5850-001-00 Rev. 2 1010-K12 2.5ML; 2010, pp. 6.

International Search Report and Written Opinion received in PCT/US18/49372, dated Oct. 29, 2018, pp. 13.

* cited by examiner

IMPLANT WITH ABILITY TO CAPTURE EXTRAVASATING FIXATION MEDIUM

RELATED APPLICATION

This application is a divisional of U.S. patent application Ser. No. 16/798,825, filed Feb. 24, 2020, which is a divisional of U.S. patent application Ser. No. 15/853,743, filed Dec. 23, 2017, now U.S. Pat. No. 10,610,365, the disclosures of which are incorporated herein by reference in their entireties.

FIELD OF THE INVENTION

The invention relates to surgical implants and their ability to capture fixation media extravasating from an implant fixation location

BACKGROUND OF THE INVENTION

Surgical implants are used to replace various joints and other anatomical features. During implantation of certain implants, it is common to use a fixation medium in order to improve adhesion and fixation of the surgical implant within an implant receiving area or cavity of a patient. For a class of implants having hybrid stems, a portion of the stem is designed to be fixed to bone with a fixation medium while another portion of the implant is designed to allow for bony ingrowth or ongrowth. During implantation of hybrid stems, excess fixation medium may be displaced from inside the cavity, which displacement is also referred to as extravasation, and flow over portions of the surgical implant that are configured to promote bone ingrowth therein. When in contact with bone ingrowth surfaces, such fixation medium may inhibit the growth of bone onto and into the implant because it covers the surface of the implant configured to receive bone ingrowth. This, in turn, reduces the volume of bone ingrowth area that is available for bone to grow into. As a result, the fixation of the implant is reduced and likelihood of failure of the implant is increased. Thus, there is a need in the art for a surgical implant that is capable of capturing excess fixation medium so as to help prevent the bone ingrowth area from being coated by fixation medium.

SUMMARY OF THE INVENTION

In an embodiment, the present invention includes an implant comprising a collar, an elongated stem and a collar-engagement feature. The collar has a proximate end, a distal end opposite the proximate end, an inner through bore extending therebetween, an exterior surface extending between the proximate and distal ends, a distal surface located adjacent the distal end and configured to abut a resected bone located adjacent an implant receiving area in a patient, and at least one recess configured to receive extravasating fixation medium, and external threads. The elongated stem has a distal tip and a proximate end opposite the distal tip, and the collar-engagement feature having internal threads. The collar is configured to attach to the elongated stem, and the external threads of the collar are rotatably engageable with the internal threads of the collar-engagement feature. The at least one recess extends from the distal surface into the collar and is located between the inner through bore and the exterior surface so as to be separated from the exterior surface.

In another embodiment, the present invention includes an implant comprising a collar, an elongated stem and a collar-engagement feature. The collar has a proximate end, a distal end opposite the proximate end, an inner through bore extending therebetween, an exterior surface extending between the proximate and distal ends, a distal surface located adjacent the distal end and configured to abut a resected bone located adjacent an implant receiving area in a patient, at least one recess configured to receive extravasating fixation medium, and external threads. The elongated stem has a distal tip and a proximate end opposite the distal tip, and the collar-engagement feature has internal threads. The at least one recess extends from the distal surface into the collar and is located between the inner through bore and the exterior surface so as to be separated from the exterior surface.

In further embodiments, the present invention includes an implant comprising a collar, an elongated stem and a collar-engagement feature. The collar has a proximate end, a distal end opposite the proximate end, an inner through bore extending therebetween, an exterior surface extending between the proximate and distal ends, a distal surface located adjacent the distal end and configured to abut a resected bone located adjacent an implant receiving area in a patient, and means for receiving extravasating fixation medium, and external threads. The elongated stem has a distal tip and a proximate end opposite the distal tip, and the collar-engagement feature has internal threads. The means for receiving extravasating fixation medium extends from the distal surface into the collar and is located between the inner through bore and the exterior surface so as to be separated from the exterior surface.

BRIEF DESCRIPTION OF THE DRAWINGS

The accompanying drawings, which are incorporated in, and constitute a part of, the specification, illustrate embodiments of the invention and, together with the description, serve to explain the objects, advantages, and principles of the invention.

DETAILED DESCRIPTION OF THE INVENTION

The present invention provides a surgical implant 10 for capturing extravasating fixation medium from an implant receiving area, also referred to simply as a cavity, of a patient. The fixation medium, which may also be referred to as cement in shorthand, may be a polymethyl methacrylate cement, a calcium phosphate cement or a glass polyalkenoate (ionomer) cement, or any other cement or non-cement substance suitable for fixation. The fixation medium is introduced to the implant 10 or to the cavity in a viscous state that allows easier application. The fixation medium then sets, or hardens, to achieve fixation. The fixation medium may include in it, among other things, one or more antimicrobial agents to combat microbial growth.

The implant 10 is configured to be implanted into a cavity. The cavity may be a reamed bone canal, an opening in bone either naturally or artificially created or enlarged, or any other suitable opening in tissue in which the implant 10 may be received. For ease of reference, the cavity described below will be a bone canal, however, this disclosure is not limited to a bone canal and other cavities are envisioned.

Figure 1:
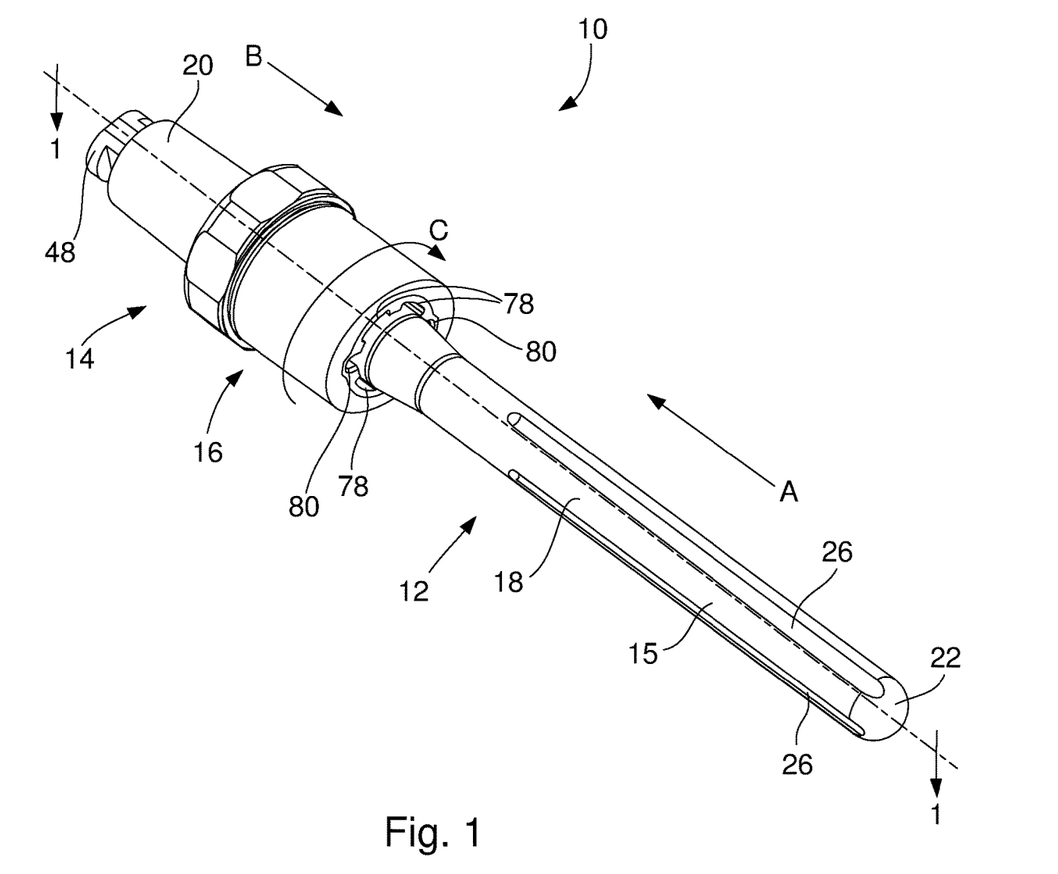
FIG. 1 is a perspective view of a surgical implant in accordance with an exemplary embodiment of the present invention.

FIGS. 1-7 depict the surgical implant 10 according to an embodiment of the present invention. The implant 10 includes an elongated stem 12, a collar-engagement feature 14, and a collar 16. FIG. 1 depicts an embodiment of the implant 10 in an assembled configuration.

Referring to FIGS. 1-3 and 7 in particular, the stem 12 includes a shank 18 configured to fit within a cavity of a patient and a head 20 configured to receive one or more types of joint assembly components known in the art. The shank 18 has a distal tip 22 and a proximate end 24 opposite the distal tip 22. In an embodiment, the distal tip 22 is rounded, while in other embodiments, the distal tip 22 may be cone-shaped, bullet-shaped, split-tipped or any other shape known in the art (see FIG. 19 for various examples of stem tips). In an embodiment, a plurality of flutes 26 are disposed on the shank 18. The plurality of flutes 26 extend from a position adjacent the distal tip 22 of the stem 12 longitudinally along the length of the shank 18 to terminate adjacent the proximate end 24 of the stem 12. In an embodiment, one or more of the plurality of flutes 26 terminate at different locations along the stem 12 with reference to one or more of the other flutes 26 (see FIG. 1). In an embodiment, the plurality of flutes 26 comprises two flutes that are located on opposite sides of the shank 18 (see FIG. 3). In other embodiments, the plurality of flutes 26 comprises four flutes located equidistant from each other to form a generally cross-like orientation (see FIG. 1). As will be evident to those skilled in the art, the flutes 26 promote adhesion and fixation of the fixation medium to the stem 12, thereby improving overall fixation of the implant 10 within the cavity of a patient. In other embodiments, the flutes 26 may be replaced by a plurality of splines (not shown) configured to promote implant fixation within the cavity of the patient.

In an embodiment, the shank 18 may have a smooth exterior 15, while in other embodiments, the exterior 15 of the shank 18 is knurled, coarse or provided with any other coating which improves fixation within the cavity of a patient. In an embodiment, the shank 18 is axially offset from the head 20 (see stems 218b, 218d depicted in FIG. 19 for instance) to facilitate placement of the implant 10 in cavities of patients having a bone structure indicating such stem. The necessity for an axially offset shank 18 can be determined by a surgeon prior to implantation.

Figure 3:
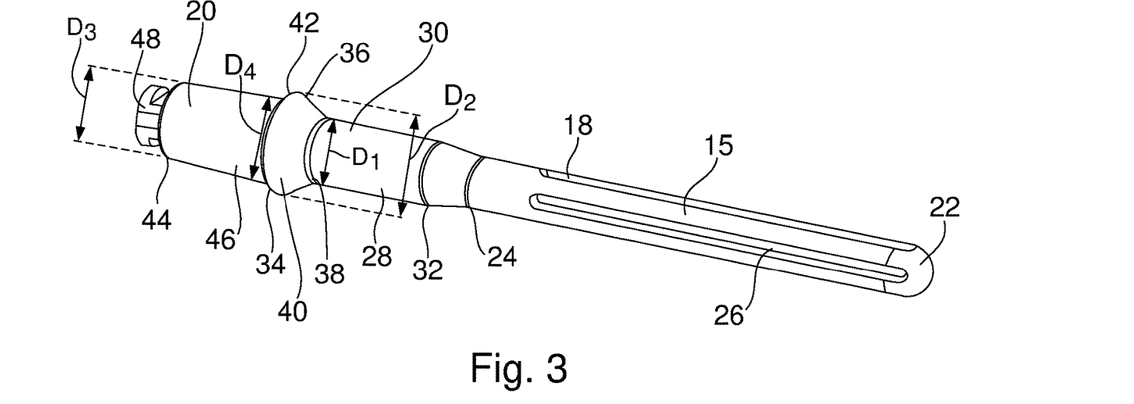
FIG. 3 is a perspective view of a stem of the implant of FIG. 1.

A seat 28 extends from the proximate end 24 of the stem 12. The seat 28 includes a proximate end 30 and a distal end 32 opposite the proximate end 30. In an embodiment, the seat 28 includes a diameter larger than the diameter of the shank 18. In other embodiments, the diameter of the seat 28 is equal to the diameter of the shank 18.

A shoulder 34 extends from the proximate end 30 of the seat 28. The shoulder 34 includes a proximate end 36, a distal end 38 opposite the proximate end 36, and an exterior surface 40 extending therebetween. In an embodiment, the shoulder 34 expands radially from the central longitudinal axis of the stem 12 so as to form a generally conical shape. In such embodiment, the shoulder 34 has a smaller diameter D1 at the distal end 38 of the shoulder 34 and a larger diameter D2 at the proximate end 36 of the shoulder 34. In an embodiment, D2 is large enough such that the proximate end 36 of the shoulder 34 forms a ridge 42 that projects radially outwardly past the diameter of the head 20. As will be described in detail below, the exterior surface 40 and the ridge 42 communicate with the collar 16 and the collar-engagement feature 14, respectively, to ensure fixed assembly of the implant 10.

The head 20 extends from the proximate end 36 of the shoulder 34. The head 20 includes a proximate end 44 having a diameter D3 and a distal end 46 having a diameter D4 opposite the proximate end 44. In an embodiment, the head 18 is generally cylindrical, however, other configurations may be utilized such as, for example, elliptical, oval, square, rectangular and the like. In an embodiment, D4 is greater than D3 so as to form a decreasing taper towards the proximate end 44 from the distal end 46, also known as a Morse taper. The degree of taper, that is, the degree of change of the diameter of the head from D4 to D3, can be varied. In such manner, embodiments of the implant 10 may be modular and capable of receiving one or more types of joint components (not shown).

An anti-rotation feature 48 is provided to prevent rotational movement of a joint component (not shown) relative to the implant 10. The anti-rotation feature 48 extends from the proximate end 44 of the head 20, and is sized and shaped so as to cooperatively communicate with a joint component (not shown). As is evident to those skilled in the art, therefore, the anti-rotation feature 48 and the head 20 facilitate the anti-rotational connection of a joint component (not shown) to the implant 10.

Figure 2:
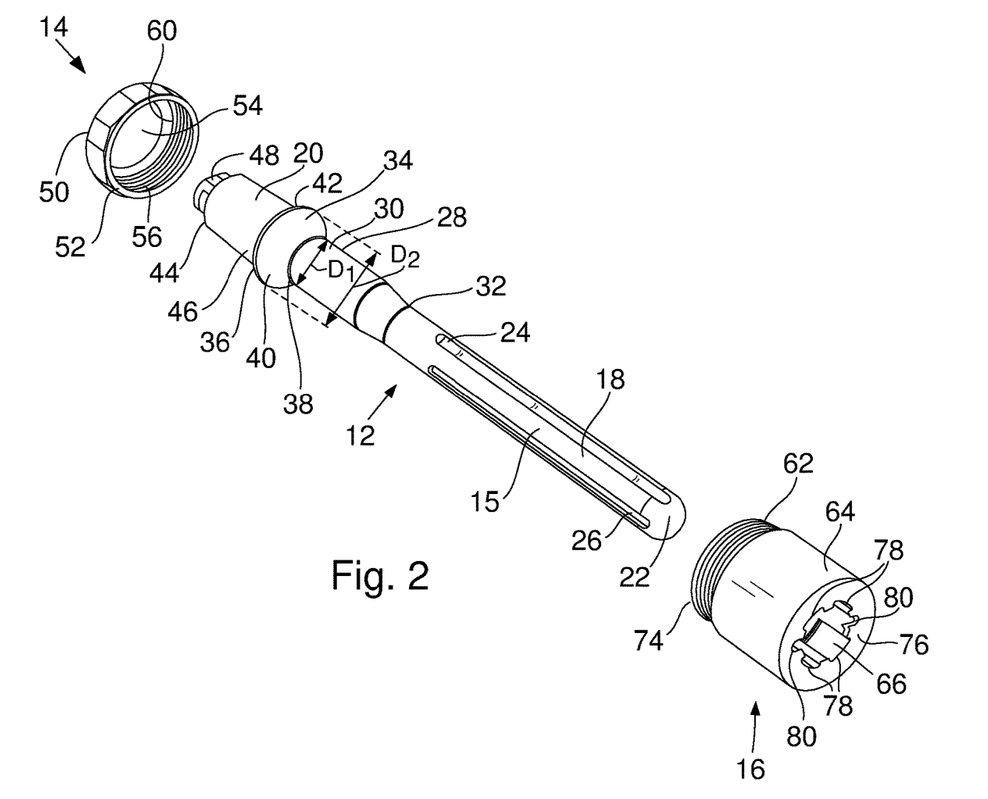
FIG. 2 is an exploded view of the implant of FIG. 1.
Figure 4:
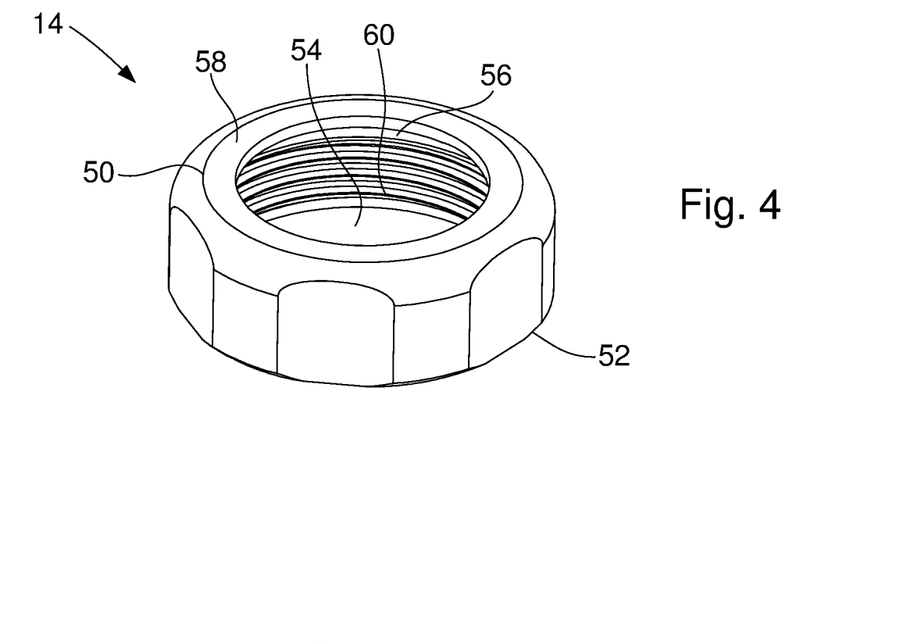
FIG. 4 is perspective view of a collar-engagement feature of the implant of FIG. 1.
Figure 5:
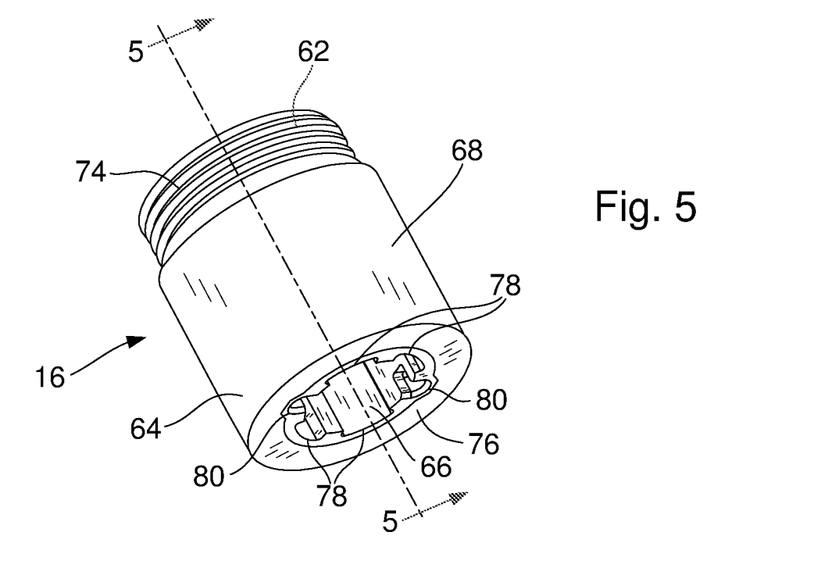
FIG. 5 is a perspective view of a collar of the implant of FIG. 1.
Figure 6:
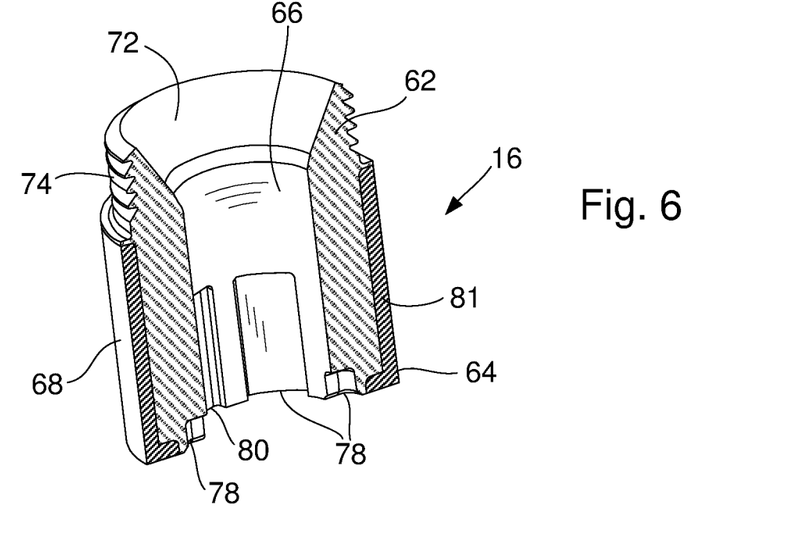
FIG. 6 is cross-sectional view of the collar of FIG. 5 along cross-sectional line 5-5 and looking in the direction of the arrows.

Referring now to FIGS. 2 and 4, the collar-engagement feature 14 includes a proximate end 50, a distal end 52 opposite the proximate end 50, and an opening 54 extending therebetween. The opening 54 is defined by an inner surface 56 and a lip 58 extending radially inwardly adjacent the proximate end 50 of the collar-engagement feature 14. In an embodiment, internal threads 60 are positioned on at least a portion of the inner surface 56. As will be described in detail below, the lip 58 communicates with the ridge 42 of the shoulder 34 and the internal threads 60 communicate with corresponding structure on the collar 16 to promote fixed assembly of the implant 10. In an embodiment, the collar-engagement feature 14 is formed integral with the stem 12. In an embodiment, the collar-engagement feature 14 may be generally hexagonal, heptagonal or octagonal to provide locations for a surgeon to grip, thereby promoting easy rotational manipulation of the collar-engagement feature 14. As will be evident to those skilled in the art, any other conventional shape may be used so long as the collar-engagement feature 14 provides a surgeon improved grip to facilitate rotation thereof.

Turning now to FIGS. 2 and 5-7, the collar 16 includes a proximate end 62, a distal end 64 opposite the proximate end 62, an inner through bore 66 extending therebetween, and an exterior surface 68. The through bore 66 is sized and shaped to receive the shank 18 and the seat 28 of the stem 12. The collar 16 further includes a generally cone-shaped inner opening 70 having a first surface 72 adjacent the proximate end 62 of the collar 16. The opening 70 is sized and shaped to correspond to the size and shape of the shoulder 34 such that the first surface 72 of the collar 16 can be fitted over and made substantially flush with the shoulder 34.

The exterior surface 68 of the collar 16 includes external threads 74 located adjacent the proximate end 62 of the collar 16. The external threads 74 correspond to internal threads 60 of the collar-engagement feature 14 to allow for threaded engagement of the collar-engagement feature 14 and the collar 16. A second surface 76 is located adjacent the distal end 64 of the collar 16. In an embodiment, the second surface 76 is configured to abut resected bone of a patient. A plurality of recesses 78 extend from the second surface 76 into the collar 16 a sufficient distance to capture fixation medium extravasating from the cavity of a patient during implantation (see FIG. 16 depicting fixation medium captured in recesses 78). The recesses 78 are generally cylindrical in shape and are arranged in a radial orientation around the second surface 76 of the collar 16. In an embodiment, one or more tool bearing recesses 80 are provided to accommodate a tool (not shown) configured to facilitate rotation or retention of the collar 16, thereby facilitating threaded engagement of the collar-engagement feature 14 and the collar 16. In an embodiment, the one or more tool bearing recesses 80 extend further into the collar 16 than the plurality of recesses 78, while in other embodiments, the one or more tool bearing recesses 80 extend an equal distance into the collar 16 as the plurality of recesses 78. In further embodiments, the plurality of recesses 78 extend further into the collar 16 than the one or more tool bearing recesses 80. In a further embodiment, the one or more tool bearing recesses 80 can be open to the through bore 66 (see FIGS. 1, 2, and 5-7), while in still other embodiments the one or more tool bearing recesses 80 are contained fully within the collar 16 (see FIGS. 11 and 13-15).

In an embodiment, the exterior surface 68 of the collar 16 can be adapted in various ways such as, for example, providing a material or coating adapted to promote bone ingrowth or adhesion/ongrowth. The material or coating may be a three-dimensional porous material 81 or porous coating as will be described in more detail below. The porous material 81 may be disposed on a portion or all of the exterior surface 68 of the collar 16. The cross-section of the collar 16 when viewed from the proximate end 62 of the collar 16 may be any conventional shape such as, for instance, circular, oval, square or other various shapes that may provide an improved fit within a cavity of a patient. The second surface 76 of the collar 16 may also be provided in various shapes. For instance, in an embodiment, the second surface 76 is flat and forms a 90-degree angle with the exterior surface 68 (see FIG. 5). In other embodiments, the second surface 76 is angled with reference to the exterior surface 68 so as to provide a sloped, cone-shape to the second surface 76 and the distal end 64 of the collar 16. In an embodiment, this cone-shape facilitates implantation of the implant 10 into the medullary canal of a patient and can be sized and shaped to fit within various portions of a patient's bone such as, for instance, the diaphysis of a patient's bone. The collar 16 may also be provided in various lengths. Decision of optimal length of collar 16 may be made by the surgeon prior to implantation of the implant 10.

Figure 19:
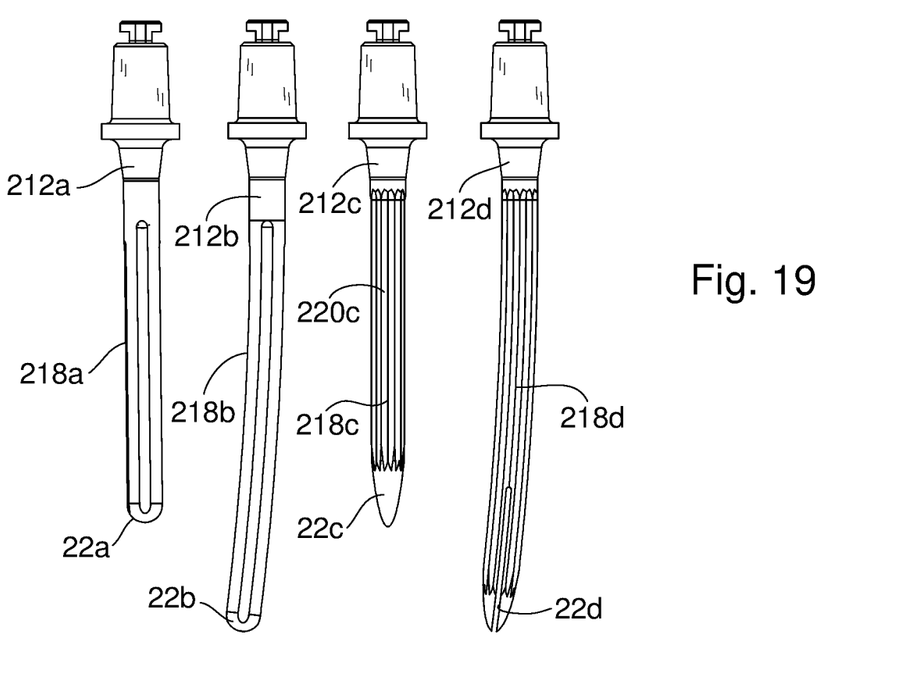
FIG. 19 is a front plan view of several embodiments of stems of the implant.

The connection mechanism of an embodiment of the implant 10 according to the present invention will now be described. In use, a surgeon will select a stem 12 of a particular size and shape depending on various factors related to the patient known prior to implantation. Such stem may, for instance, be straight or bowed, fluted or splined, and have a single or split tip. FIG. 19 depicts various embodiments of stems that can be used in conjunction with the present invention, as will be described in more detail below.

Once the stem 12 has been selected, a particularly sized and shaped collar 16 is then selected that corresponds to the dimensions of the stem 12 and the mating bone surface. Selection of the collar 16 determines the selection of collar-engagement feature 14. The size and pitch of the external threads 74 of the collar 16 determine the size and pitch of the corresponding internal threads 60 of the collar-engagement feature 14. As will be evident to those skilled in the art, the collar 16 and the collar-engagement feature 14 must be capable of fitting over the shank 18 and seat 28 of the stem 12 and over the head 20, respectively.

Figure 7:
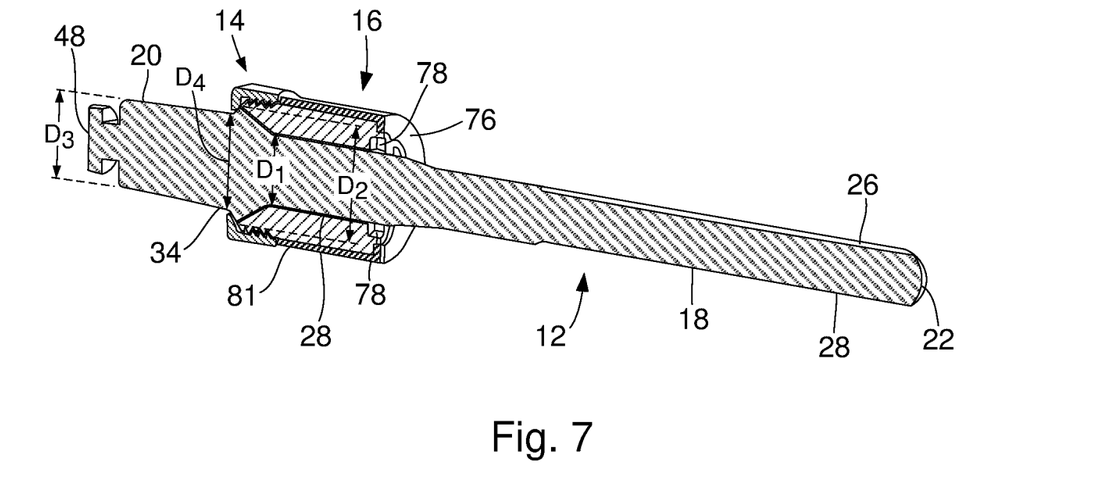
FIG. 7 is a cross-sectional view of an assembled surgical implant of FIG. 1 along cross-sectional line 1-1 and looking in the direction of the arrows.

Once the proper size stem 12, collar-engagement feature 14 and collar 16 have been selected, they must be aligned according to the orientation depicted in FIGS. 1, 2 and 7. The collar 16 is positioned over the distal tip 22 of the shank 18 and is then translated longitudinally along the shank 18 until the collar 16 travels over the seat 28 and the first surface 72 of the cone-shaped opening 70 rests adjacent the shoulder 34 (see arrow A in FIG. 1 depicting movement of the collar 16). Collar-engagement feature 14 is positioned over the head 20 and translated longitudinally along head 20 until the lip 58 of the collar-engagement feature 14 rests adjacent the ridge 42 of the shoulder 34 (see arrow B in FIG. 1 depicting movement of the collar-engagement feature 14). Once both the collar 16 and the collar-engagement feature 14 are translated as described above, the internal threads 60 of the collar-engagement feature 14 abut the external threads 74 of the collar 16. Next, the collar-engagement feature 14 and the collar 16 are threadedly engaged via rotating either the collar-engagement feature 14 or the collar 16 such that the internal threads 60 and external threads 74 interact with each other (one embodiment of this connection mechanism is shown by arrow C in FIG. 1 depicting rotational movement of the collar 16). In an embodiment, the collar-engagement feature 14 is restrained while a rotational force is applied to the collar 16. Conversely, the collar 16 may be restrained while a rotational force is applied to the collar-engagement feature 14 or, in a still further embodiment, both the collar 16 and the collar-engagement feature 14 may be rotated simultaneously in opposing directions. In each of these three embodiments, rotational force is applied until the collar-engagement feature 14 and the collar 16 are locked together. In an embodiment, a tool (not shown) can be introduced into the tool bearing recesses 80 to facilitate rotation or retention of the collar 16. During such threaded rotation, the ridge 42 and lip 58 function to ensure fixed connection and proper positioning of the collar 16 and the collar-engagement feature 14 along the length of the stem 12. Once assembled, the implant 10 is/can be implanted into a patient.

FIGS. 8-12 depict an alternative embodiment of the present invention labeled implant 110. Implant 110 is substantially similar to implant 10 in general construction and use. As such, discussion of similarities between the implant 10 and the implant 110 will be omitted. Where necessary, similar elements will be labeled with the same reference number offset by 100. For clarity, where elements of the implant 110 differ from the elements of the implant 10, such elements will be given an odd reference number.

Referring now to FIGS. 8-10 and 12, the implant 110 includes an elongated stem 112 having a shank 118 and a head 120 and a collar 117 adapted to be rotatably fixed on the stem 112. A connection member 119 is positioned between the shank 118 and the head 120. The connection member 119 has a proximate end 121 and a distal end 123 opposite the proximate end 121. The connection member 119 has a diameter D5 adjacent the proximate end 121 and a diameter D6 adjacent the distal end 123. In an embodiment, the distal end 123 of the connection member 119 includes a flared seat 125 adjacent the shank 118. One or more connection elements 127 are positioned on the connection member 119. The connection elements 127 are configured to communicate with the collar 117 to achieve fixed assembly of the implant 110, as will be discussed in more detail below. In an embodiment, connection elements 127 are flanges positioned opposite each other (see FIGS. 9, 10 and 12). In other embodiments, other mechanisms of connection are envisioned such as, for instance, an interference fit, a snap fit or any other conventional connection mechanism capable of connecting the collar 117 to the stem 112.

In an embodiment, diameter D5 is larger than diameter D6, thereby creating a ledge 129 which acts as a stop for the collar 117. In this manner, the collar 117 can be fitted over the shank 118 and translated along the length of the stem 112 until the collar 117 reaches the ledge 129. In other embodiments, diameters D5 and D6 are equal and the collar 117 includes additional structure (not shown) that functions as a stop to ensure the collar 117 is positioned at the proper location along the stem 112.

Turning to FIGS. 8-9 and 11-12, the collar 117 has a proximate end 131, a distal end 133 opposite the proximate end 131, an inner through bore 135 extending therebetween and an exterior surface 137. The through bore 135 is sized and shaped to fit over the shank 118 and the one or more connection elements 127. The through bore 135 includes at least one connection receiving element 139 adjacent the proximate end 131 of the collar 117. The at least one connection receiving element 139 must correspond to the one or more connection elements 127. Thus, in an embodiment wherein connection elements 127 are flanges, the at least one connection receiving element 139 is one or more corresponding threads sized and shaped to receive the flanges and lock them in place. In an embodiment, the through bore 135 includes an inner flared region 141 that corresponds to the flared seat 125 of the connection member 119.

Figure 11:
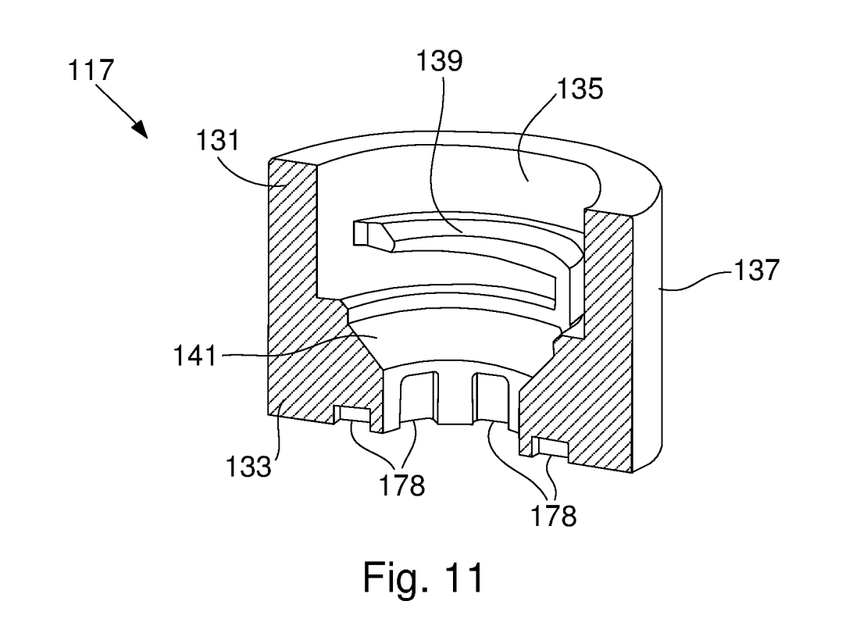
FIG. 11 is a cross-sectional view of a collar of the implant of FIG. 8 along cross-sectional line 9-9 and looking in the direction of the arrows.
Figure 12:
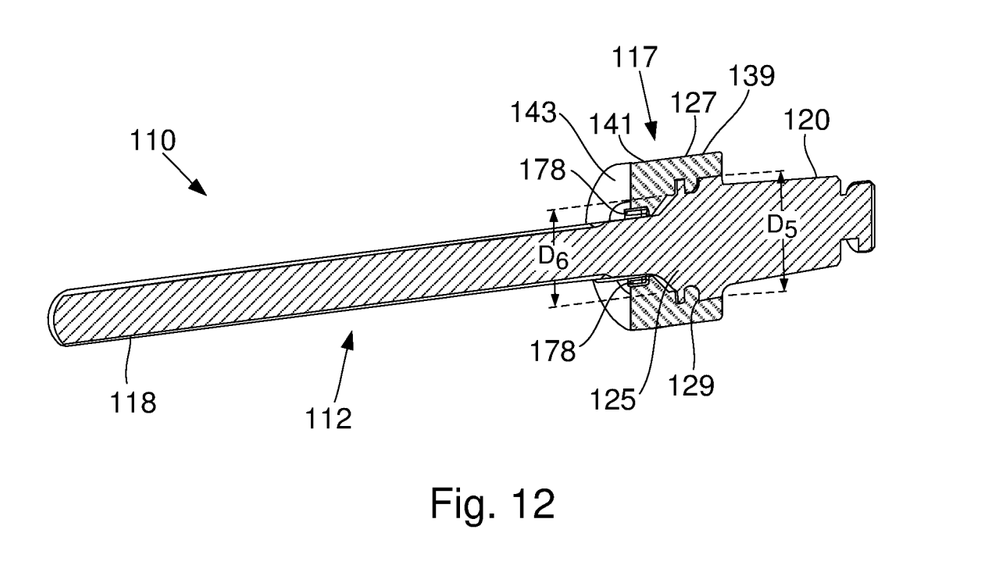
FIG. 12 is a cross-sectional view of an assembled surgical implant of FIG. 8 along cross-sectional line 8-8 and looking in the direction of the arrows.
Figure 13:
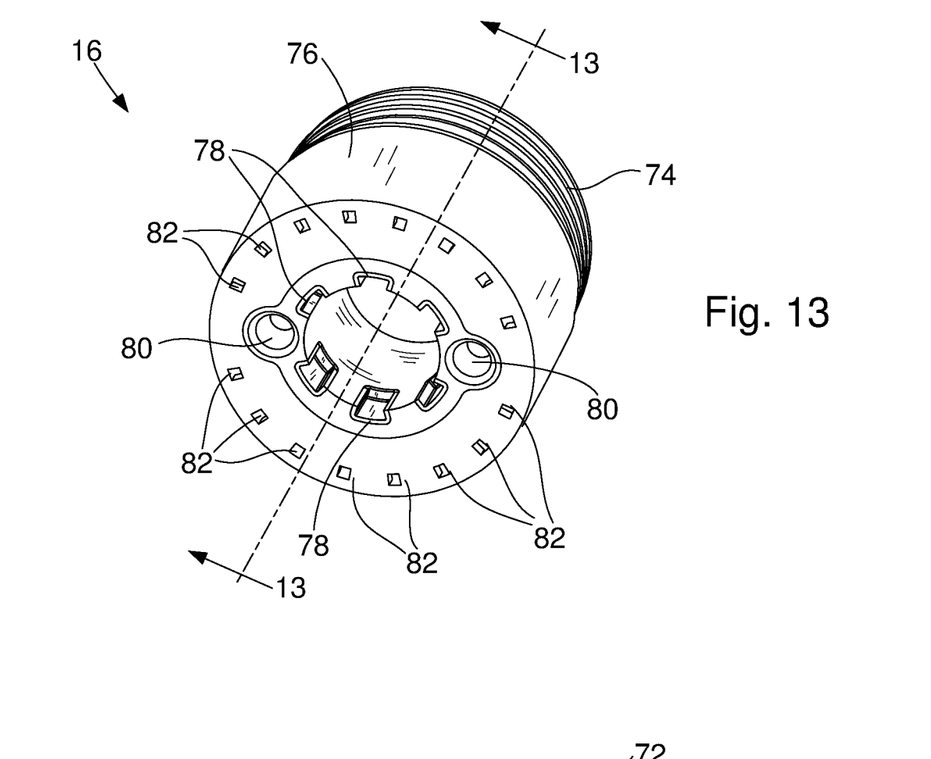
FIG. 13 is a bottom perspective view of the collar according to an embodiment of the present invention.
Figure 14:
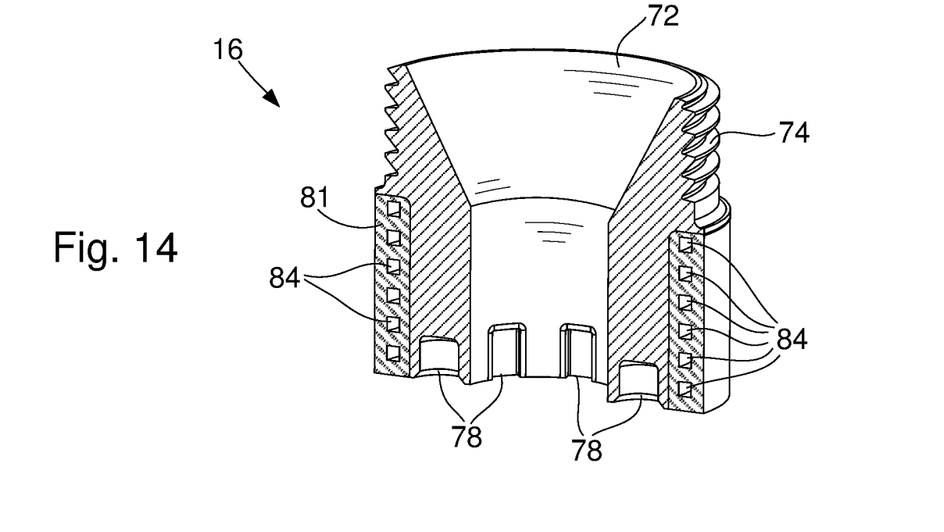
FIG. 14 is a cross-sectional view of another embodiment of the collar of the implant along cross-sectional line 13-13 and looking in the direction of the arrows.

A surface 143 is located adjacent the distal end 133 of the collar 117. In an embodiment, the surface 143 is configured to abut resected bone of a patient. A plurality of recesses 178 extend from the surface 143 into the collar 117 a sufficient distance to capture fixation medium extravasating from a cavity of a patient during implantation. The recesses 178 are generally cylindrical in shape and are arranged in a radial orientation on the surface 143 of the collar 117. One or more tool bearing recesses 180 are provided to accommodate a tool (not shown) configured to facilitate rotation and/or retention of the collar 117, thereby allowing assembly of the implant 110.

Figure 8:
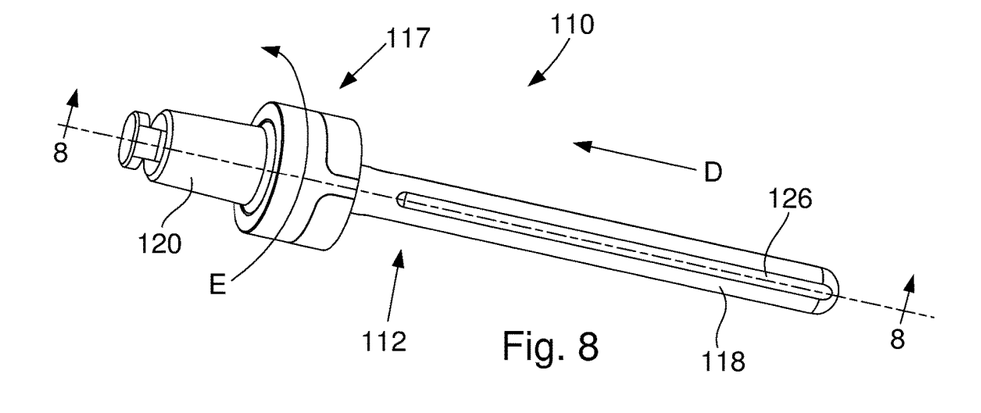
FIG. 8 is a perspective view of a surgical implant in accordance with another exemplary embodiment of the present invention.
Figure 9:
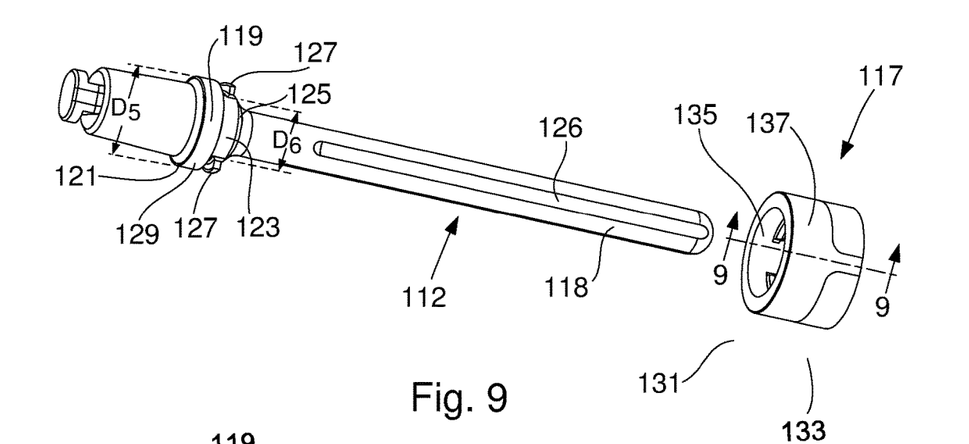
FIG. 9 is an exploded view of the implant of FIG. 8.
Figure 10:
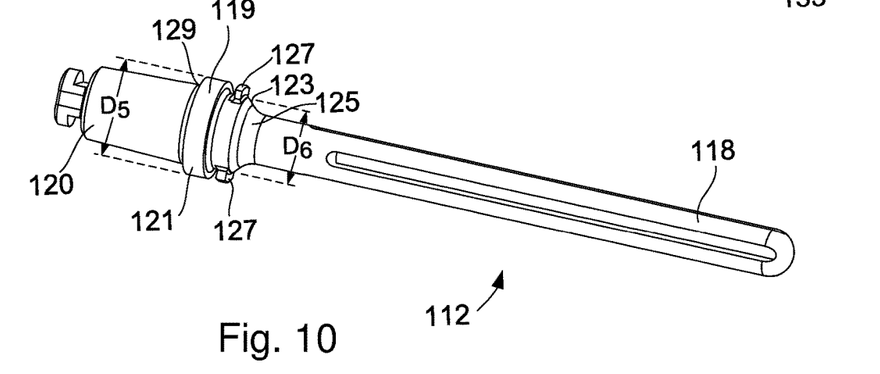
FIG. 10 is a perspective view of a stem of the implant of FIG. 8.

The connection mechanism of an embodiment of the implant 110 according to the present invention, which can also be referred to as a "bayonet" style connection, will now be described. Once a surgeon has selected the particular stem 112 as described above in reference to stem 12, an appropriately sized collar 117 is selected that corresponds to the dimensions of the chosen stem 112 and the bone mating surface of a patient's bone. The collar 117 will include the at least one connection receiving element 139 that corresponds to and is adapted to interact with the one or more connection elements 127 of the chosen stem 112. In an embodiment, the one or more connection elements 127 are flanges and the at least one connection receiving element 139 is one or more threads capable of receiving the flanges. In this embodiment, the collar 117 is fitted over the shank 118 and translated along the length of the stem 112 until the collar 117 reaches the ledge 129 of the connection member 119 (see arrow D in FIG. 8 depicting movement of the collar 117). Once the collar 117 reaches the ledge 129, the collar 117 may be threadedly engaged with the stem 112 by applying a rotational force to the collar 117 while the stem 112 is restrained so that the flanges of the one or more connection elements 127 travel down the one or more threads of the at least one connection receiving element 139 (see arrow E in FIG. 8 depicting movement of the collar 117). Conversely, collar 117 may be restrained while a rotational force is applied to the stem 112 or, in some embodiments, both the collar 117 and the stem 112 may be rotated simultaneously in opposing directions. In an embodiment, a tool (not shown) can be introduced into the tool bearing recesses 180 to facilitate rotation and/or retention of the collar 117.

In an embodiment, the collar 117 or the stem 112 is turned three-quarters of a full rotation to lock the stem 112 and the collar 117. In another embodiment, the collar 117 and the stem 112 each rotate to a combined magnitude of three-quarters of a full rotation to lock the stem 112 and the collar 117. In other embodiments, more or less rotation is necessary to lock the stem 112 and the collar 117. The flared seat 125 and the inner flared region 141 ensure that there is space between the collar 117 and the stem 112 to allow for rotation. Once fully rotated, the implant 110 is in an assembled state and is/can be implanted into a patient.

The mechanism of fixation medium capture will now be described with reference to FIGS. 13-16. FIGS. 13-16 depict the implant 10, however, the following mechanism is similarly applicable to implant 110. As described above, the plurality of recesses 78 are disposed throughout the second surface 76. In an embodiment, additional vertical recesses 82 may be provided so as to receive more fixation medium if necessary. The vertical recesses 82 are sized and shaped to accommodate extravasating fixation medium. In a further embodiment, horizontal recesses 84, which are sized and shaped to accommodate extravasating fixation medium, are connected to vertical recesses 82 so as to receive additional fixation medium if necessary. As will be evident to one of ordinary skill in the art, each of the horizontal recesses 84 must be connected to at least one of the vertical recesses 82 to provide a pathway for extravasating fixation medium. In an embodiment, the recesses 78 are spaced equidistantly in a radial orientation throughout the collar 16. In other embodiments, the recesses 78 may be arranged randomly throughout the collar 16.

In practice, the cavity may be pre-machined in order to prepare the cavity for implantation of the implant 10. Fixation medium is then added to the cavity. Alternatively, fixation medium made be added directly to the implant 10, 110 and allowed to set until it exhibits a malleable putty-like consistency. The implant 10, 110 is then implanted into the patient by aligning the shank 18 with the cavity and inserting the implant 10, 110 into the cavity. During the insertion process, excess fixation medium will be forced to extravasate from the cavity.

Figure 15:
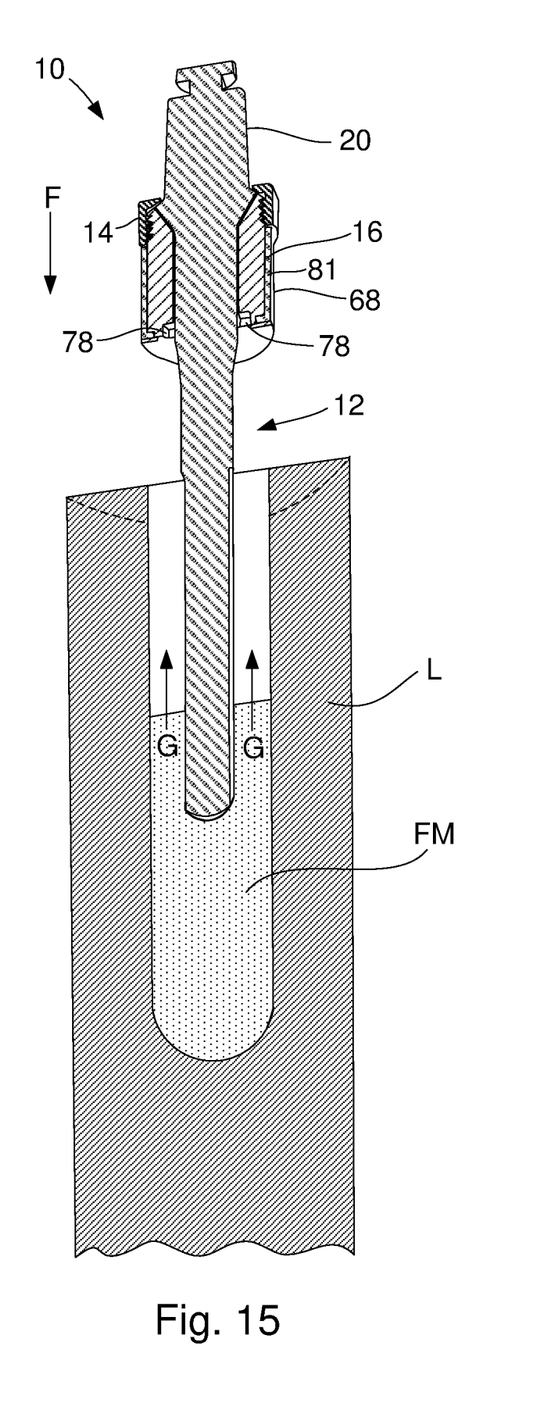
FIG. 15 is a cross-sectional view of the implant of FIG. 1 along cross-sectional line 1-1 during insertion of the implant into an implant receiving area pre-charged with fixation medium.
Figure 16:
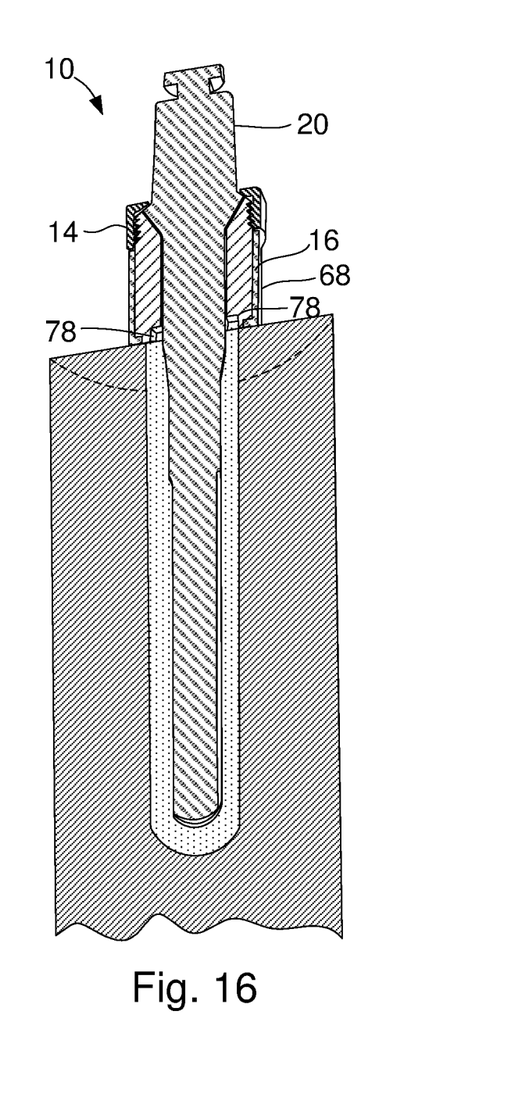
FIG. 16 is a cross-sectional view of the implant of FIG. 1 along cross-sectional line 1-1 after insertion of the implant into an implant receiving area pre-charged with fixation medium.

FIG. 15 depicts the implant 10 during insertion into a cavity of a long bone L that has been pre-charged with fixation medium FM. The implant 10 causes displacement of the fixation medium FM previously introduced to the cavity (see arrow F depicting movement of the implant 10 and arrows G depicting movement of the fixation medium FM). Once the second surface 76 contacts the extravasating fixation medium, the fixation medium FM is forced into and taken in by the plurality of recesses 78. This reduces or eliminates the amount of fixation medium FM that can escape from the cavity to reach the exterior surface 68 of the collar 16.

FIG. 16 depicts the implant 10 inserted into a cavity of a long bone L that has been pre-charged with fixation medium FM. The implant 10 has displaced the fixation medium FM and caused the fixation medium FM to extravasate from the cavity of the long bone L. The fixation medium FM has been taken in by the plurality of recesses 78. In this manner, the exterior surface 68 of the collar 16 retains a suitable bone ingrowth region. As will be evident to one of ordinary skill in the art, a substantially similar process occurs during insertion of the implant 110.

Figures 17, 18:
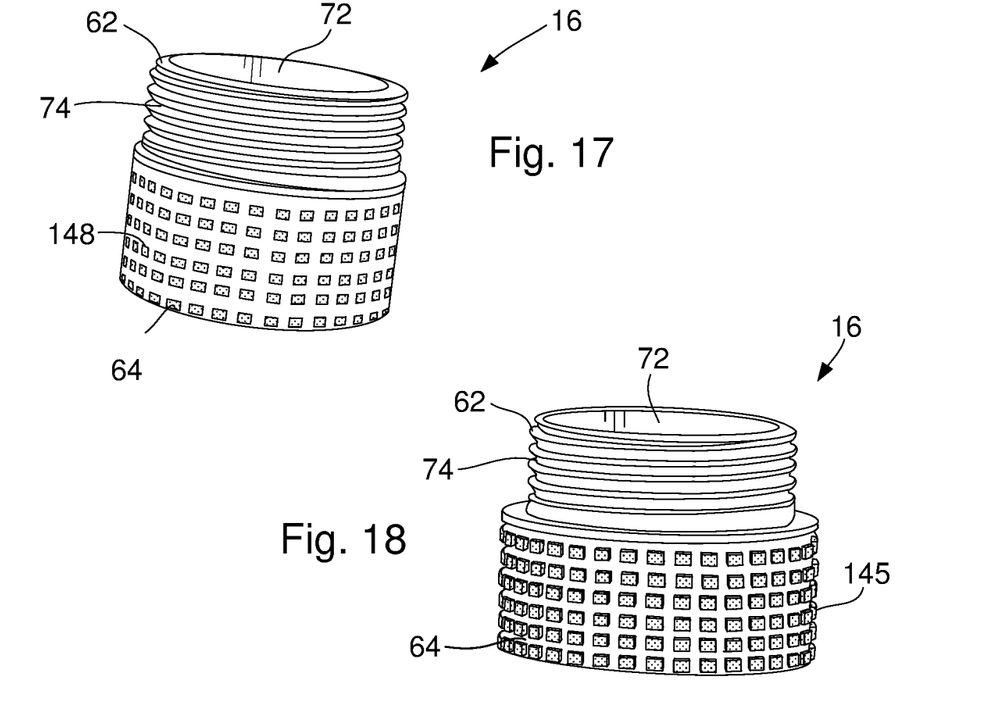
FIG. 17 is a perspective view of a further embodiment of the collar of the implant.
FIG. 18 is a perspective view of a further embodiment of the collar of the implant.

FIGS. 17 and 18 depict various embodiments of exterior surfaces or coatings to be used in conjunction with the collar 16 or the collar 117. In an embodiment, the exterior surfaces 68, 137 of the collars 16, 117, respectively, can be formed of or coated with a three-dimensional porous structure 81. The porosity may be varied to optimize bone ingrowth and bone apposition on the collars 16, 117. The porous structure may further include randomness or have areas for soft tissue ingrowth and other areas for hard tissue ingrowth.

In an embodiment, a porous pattern 145, such as, for instance, a waffle-pattern, may be used on the exterior surfaces 68, 137 to further facilitate bone ingrowth and bone apposition on the collars 16, 117. In other embodiments, other conventional patterns may be used. In an embodiment, the exterior surfaces 68, 137 of the collars 16, 117 are coated with various bone-growth factors, such as hydroxyapatite or other substances known to stimulate bone growth. In other embodiments, the exterior surfaces 68, 137 of the collars 16, 117 are coated with one or more antimicrobial, antibacterial, antiviral, antifungal coatings or other substances known to inhibit growth of microbial life. Similarly, the foregoing bone growth stimulating substances and the antimicrobial substances can be formed integral with the porous structure 81 or dispersed therein. The porous structure 81 and coatings may be bioresorbable or configured to not degrade within the body.

FIG. 19 depicts various embodiments of stems, which are labeled 212a— 212d for clarity, with differing shanks that can be incorporated into the implants 10, 110. The leftmost stem 212a includes a straight shank 218a with a rounded distal tip 22a. Stem 212b includes an offset or bowed shank portion 218b with a rounded distal tip 22b to be used in procedures where the cavity indicates such the shank 218b. Stem 212c depicts a shank portion 218c having splined canals 220c instead of flutes similar to flutes 26 and a pointed distal tip 22c instead of the rounded distal tip 22. Stem 212d incorporates a bowed shank portion 218d similar to stem 212b, but with a slotted tip 22d.

Various modifications may be made to the scope of the present invention without departing from the spirit thereof. For instance, the collars 16, 117 may be configured with one or more areas of internal space (not shown) connecting one or more of the plurality of recesses 78, 178 and additional recesses 82, 84 to each other, thereby increasing the maximum volume of fixation medium that can be taken in by the implants 10, 110.

Other embodiments of the invention will be apparent to those skilled in the art from consideration of the specification and practice of the invention disclosed herein. It is intended that the embodiments described below be considered as exemplary only, with a true scope and spirit of the invention being indicated by the appended claims. Moreover, none of the features disclosed in this specification should be construed as essential elements, and therefore, no disclosed features should be construed as being part of the claimed invention unless the features are specifically recited in the claims. In addition, it should be understood that any of the features disclosed on any particular embodiment may be incorporated in whole or in part on any of the other disclosed embodiments.

What is claimed is:

1. An implant comprising:
   a collar having a proximate end, a distal end opposite the proximate end, an inner through bore extending therebetween, an exterior surface extending between the proximate and distal ends, a distal surface located adjacent the distal end for directly contacting a resected bone located adjacent an implant receiving area in a patient, and at least one recess configured to receive extravasating fixation medium, and external threads,
   an elongated stem having a distal tip and a proximate end opposite the distal tip, and a collar-engagement feature having internal threads,
   wherein the collar is configured to attach to the elongated stem, and the external threads of the collar are rotatably engageable with the internal threads of the collar-engagement feature, and
   wherein the at least one recess extends from the distal surface into the collar and is located between the inner through bore and the exterior surface so as to be separated from the exterior surface, the at least one recess including a plurality of recesses, and wherein the collar is configured with one or more areas of internal space connecting two or more of the plurality of recesses, whereby the volume of fixation medium that can be taken in by the implant is maximized.

2. The implant of claim 1, wherein the stem includes a radially projecting shoulder.

3. The implant of claim 2, wherein the collar and the collar-engagement feature are configured to be assembled over the shoulder prior to insertion of the implant into an implant-receiving area of a patient.

4. The implant of claim 1, wherein the exterior surface of the collar includes a three-dimensional porous structure having a varied porosity to optimize bone ingrowth and bone apposition on the collar.

5. The implant of claim 1, wherein the at least one recess is generally cylindrical in shape.

6. An implant comprising:
a collar having a proximate end, a distal end opposite the proximate end, an inner through bore extending therebetween, an exterior surface extending between the proximate and distal ends, a distal surface located adjacent the distal end for directly contacting and configured to abut a resected bone located adjacent an implant receiving area in a patient, at least one recess configured to receive extravasating fixation medium, and external threads,
an elongated stem having a distal tip and a proximate end opposite the distal tip, and a collar-engagement feature having internal threads, and
wherein the at least one recess extends from the distal surface into the collar and is located between the inner through bore and the exterior surface so as to be separated from the exterior surface, the at least one recess including a plurality of recesses, and wherein the collar is configured with one or more areas of internal space connecting two or more of the plurality of recesses, whereby the volume of fixation medium that can be taken in by the implant is maximized.

7. The implant of claim 6, wherein the collar is configured to attach to the elongated stem, and the external threads of the collar are rotatably engageable with the internal threads of the collar-engagement feature.

8. The implant of claim 6, wherein the implant includes a radially projecting shoulder over which the collar-engagement feature and the collar can be fixed.

9. The implant of claim 8, wherein the collar and the collar-engagement feature are configured to be assembled over the shoulder prior to insertion of the implant into an implant-receiving area of a patient.

10. The implant of claim 6, wherein the exterior surface of the collar includes a three-dimensional porous structure having a varied porosity to optimize bone ingrowth and bone apposition on the collar.

11. The implant of claim 6, wherein the at least one recess is generally cylindrical in shape.

12. An implant comprising:
a collar having a proximate end, a distal end opposite the proximate end, an inner through bore extending therebetween, an exterior surface extending between the proximate and distal ends, a distal surface located adjacent the distal end for directly contacting and configured to abut a resected bone located adjacent an implant receiving area in a patient, and a means for receiving extravasating fixation medium, and external threads,
an elongated stem having a distal tip and a proximate end opposite the distal tip, and
a collar-engagement feature having internal threads,
wherein the means for receiving extravasating fixation medium extends from the distal surface into the collar and is located between the inner through bore and the exterior surface so as to be separated from the exterior surface, the means for receiving extravasating fixation medium including at least one recess configured to receive extravasating fixation medium, wherein the at least one recess includes a plurality of recesses, the collar being configured with one or more areas of internal space connecting two or more of the plurality of recesses, whereby the volume of fixation medium that can be taken in by the implant is maximized.

13. The implant of claim 12, wherein the collar is configured to attach to the elongated stem, and the external threads of the collar are rotatably engageable with the internal threads of the collar-engagement feature.

14. The implant of claim 12, wherein the implant includes a radially projecting shoulder over which the collar-engagement feature and the collar can be fixed.

15. The implant of claim 14, wherein the collar and the collar-engagement feature are configured to be assembled over the shoulder prior to insertion of the implant into an implant-receiving area of a patient.

16. The implant of claim 12, wherein the at least one recess is generally cylindrical in shape.

* * * * *